United States Patent
Giri et al.

(12) 
(10) Patent No.: US 6,242,602 B1
(45) Date of Patent: Jun. 5, 2001

(54) ONE POT SYNTHESIS OF 5,10-DIHYDROPHENAZINE COMPOUNDS AND 5,10-SUBSTITUTED DIHYDROPHENAZINES

(75) Inventors: Punam Giri; Harlan J. Byker; Kelvin L. Baumann, all of Holland, MI (US)

(73) Assignee: Gentex Corporation, Zeeland, MI (US)

( * ) Notice: Subject to any disclaimer, the term of this patent is extended or adjusted under 35 U.S.C. 154(b) by 0 days.

(21) Appl. No.: 09/280,396

(22) Filed: Mar. 29, 1999

(51) Int. Cl.$^7$ ...................... C07D 241/46; C07D 241/48
(52) U.S. Cl. ............................................. 544/347; 544/347
(58) Field of Search ................................................. 544/347

(56) References Cited

U.S. PATENT DOCUMENTS

| | | | |
|---|---|---|---|
| 2,292,808 | 8/1942 | Waterman et al. .................. | 260/267 |
| 2,332,179 | 10/1943 | Soule .................................. | 260/267 |

FOREIGN PATENT DOCUMENTS 50-95281  7/1975  (JP) .

OTHER PUBLICATIONS

J. S. Morley, The Chemotherapy of Filariasis. Part II. Monacyl Derivatives of 5: 10–Dihydro–and trans–1: 2: 3: 4: 5: 10: 11: 12–Octahydrophenazine, J. Chem. Soc., 1952, pp. 4008–4014.

Henry Gilman et al., "The Direct Preparation of Some Dihydro and Other Phenazine Derivatives", Journal of American Chemical Society, Dec. 5, 1957, vol. 79, pp. 6178–6179.

G. F. Bettinetti et al., "Synthesis of 5, 10–Dialkyl-5, 10–dihydrophenazines", Synthesis, Nov. 1976, pp. 748–749.

B. M. Mikhailov et al., "Metal Compounds of Phenazine and Their Transformations", 1950, Chemical Abstracts, vol. 44, pp. 9452–9453.

Axel Kistenmacher et al., "Synthesis of New Soluble Triphenodithiazines and Investigation of Their Donor Properties", Chem. Ber., 1992, 125, pp. 1495–1500.

Akira Sugimoto et al., "Preparation and Properties of Electron Donor Acceptor Complexes of the Compounds Having Capto–Dative Substituents", Mar.–Apr. 1989, vol. 26, pp. 435–438.

*Primary Examiner*—Richard L. Raymond
*Assistant Examiner*—Ben Schroeder
(74) *Attorney, Agent, or Firm*—Brian J. Rees; Factor & Partners, LLC

(57) ABSTRACT

Dihydrophenazines and bis(dihydrophenazines) are prepared in high yield under commercially viable reaction conditions by reacting a catechol with a 1,2-diaminoaryl compound, wherein either the catechol or the 1,2-diaminoaryl compound is provided in at least 50% molar stoichiometric excess. The product may be oxidized to the corresponding phenazine, but is preferably derivatized at one or both of the 5,10-positions to form a monosubstituted or disubstituted dihydrophenazine or bis(dihydrophenazine). Most preferably, 5,10-dialkyl-5,10-dihydrophenazines are prepared starting from catechol and 1,2-diaminoaryl compound in a one pot synthesis. The products are useful as dyes, and in particular as chromophores in electrochromic systems.

49 Claims, No Drawings

ONE POT SYNTHESIS OF 5,10-DIHYDROPHENAZINE COMPOUNDS AND 5,10-SUBSTITUTED DIHYDROPHENAZINES

TECHNOLOGICAL FIELD

The present invention pertains to a low cost method of preparing dihydrophenazine and dihydrophenazine derivatives, including substituted phenazines.

DESCRIPTION OF THE RELATED ART

Phenazines occupy a somewhat unique status in the field of organic chemistry. In his abortive attempt to synthesize quinine, Sir William Henry Perkin instead synthesized mauveine, an impure mixture of substituted phenazines and other compounds, which became the first successful synthetic dye. This synthesis, in the mid-19th century, is regarded as the beginning of the synthetic organic chemical industry.

In the phenazine series of dyestuffs, while consistency of product color, shade, and dyeing ability has been important, purity in the sense of preparing or isolating well defined compounds has not. See, e.g., "Azine Dyes", J. Clyde Conger, Kirk Othmer CONCISE ENCYCLOPEDIA OF CHEMICAL TECHNOLOGY,© 1985, p. 142. The base structure shared by the phenazine dyes, phenazine itself,

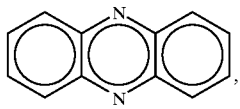

has been prepared by several methods, in varying degrees of purity, and with some degree of difficulty. For example, early syntheses included the reaction of nitrobenzene with aniline in the presence of caustic. However, the reaction is dangerous and difficult to control, and the yield of the initial product, phenazine oxide, is low. Large quantities of azobenzene are formed. The phenazine oxide can be reduced to phenazine. Phenazine has also been prepared by the reduction of 1,1'-dinitrodiphenylamine. Eckert et al., Monatshefte für Chemie, 1914, pp. 1153–55.

In U.S. Pat. No. 2,292,808, phenazine is manufactured by the cyclization of ortho-nitrodiphenylamine, itself prepared by the lead oxide oxidation of ortho-amino diphenylamine. The cyclization is effected with a zero valent metal or low valent metal oxide such as chromous oxide or lead suboxide, which act as oxygen acceptors. The reaction involves the use of a nitro group-substituted organic compound which is potentially dangerous, and generates large quantities of environmentally suspect heavy metal-containing waste products.

Phenazine and 5,10-dihydrophenazine are prepared from catechol and o-phenylenediamine by J. S. Morley, J. CHEM. SOC. (1952), p. 4008–4014, following an earlier procedure reported by Ris, BER., 1886 (19), p. 2206. In this reaction, catechol and o-phenylenediamine are heated under pressure in a sealed tube at 200–210° C. for 35–40 hours. The yield is modest, and somewhat lower after purification, ca. 60% overall. The product may be converted to phenazine by standard methods, for example by sublimation in a stream of oxygen. Dihydrophenazine is notoriously sensitive to oxidation. The method of Morely and Ris suffers from the disadvantage that the process is not amenable to large scale production, and from the further disadvantage that considerable quantities of unidentified impurities are formed.

In Wataya published Japanese application JP 48-144440 (laid open Jul. 29, 1975), 2-nitrophenylenediamine or substituted 2-nitrophenylenediamines are cyclized with the aid of highly basic metal alcoholates in dimethylsulfoxide solvent. The latter solvent is relatively expensive. However, Wataya indicates that other solvents, for example benzene, toluene, ethers, and hydroxylic solvents such as aliphatic alcohols, fail to work, or produce products only very slowly or in low yield. Purification from dimethylsulfoxide solvent-based reactions is difficult, requiring chromatographic methods.

All the foregoing syntheses are difficult on a commercial scale, involve use of expensive reagents, or generate undesirable byproducts. These difficulties may be reflected in the very high cost of phenazine, averaging ca. $1000/Kg or more. However, pure phenazine and dihydrophenazine and their derivatives have become increasingly useful, not only as dyestuffs, or dyestuff intermediates, but as pharmaceuticals and other products. For example, many 5,10-disubstituted dihydrophenazines, and 5,10-disubstituted dihydrophenazines bearing ring substituents in the 1–4 and/or 6–9 positions have been shown to exhibit electrochromic behavior, and can be used as chromophores in applications such as electrically dimmable mirrors (electrochromic mirrors), windows, and the like.

Importantly, some ring-substituted dihydrophenazines, when employed with other electrochromophores, can produce a color which varies from colorless to very dark gray without significant color shift during transitioning. Compositions such as these, and electrochromic devices containing them, are disclosed in copending U.S. patent application Ser. No. 08/832,596 filed Apr. 2, 1997, and entitled: Improved Electrochromic Medium Capable Of Producing A Preselected Color, herein incorporated by reference. To be useful in such applications, unlike the phenazine dyes of the nineteenth century, the electrochromophores must be produced in a high degree of purity. Unfortunately, the synthetic route to these ring-substituted dihydrophenazines begins by reducing expensive and not widely available phenazine. Moreover, ring-substituted dihydrophenazines such as alkyl, ring substituted-dihydrophenazines are inaccessible by this route, and are not presently commercially available.

It would be desirable to prepare dihydrophenazine, substituted dihydrophenazines, and analogous phenazines by a simple procedure, in acceptable yield, which procedure can be commercially practiced in large scale without the use of nitro group-substituted organic compounds, without requiring a pressurized autoclave, and without significant use of transition or heavy metals. It would be further desirable to provide a one pot synthesis of ring-substituted dihydrophenazines without employing expensive phenazine as starting material. It would be yet further desirable to provide a lower cost route to phenazine.

DISCLOSURE OF INVENTION

It has now been surprisingly discovered that dihydrophenazine and substituted dihydrophenazines can be prepared simply and in acceptable yields, by the solvent mediated reaction of substituted or unsubstituted catechols with substituted or unsubstituted 1,2-diaminoaryl compounds, particularly 1,2-diaminobenzenes (o-phenylenediamines). In addition to dihydrophenazines, bis[dihydrophenazines] can also be prepared. The products can be readily oxidized to the corresponding phenazines, and may optionally be derivatized at the 5 and/or 10 positions without oxidation to prepare N-substituted dihydrophenazines.

DESCRIPTION OF THE PREFERRED EMBODIMENTS

The phenazines and dihydrophenazines produced by the subject invention process preferably correspond to the formulas I and II, respectively:

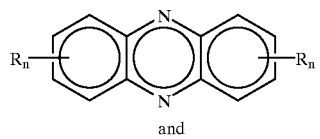

(I)

and

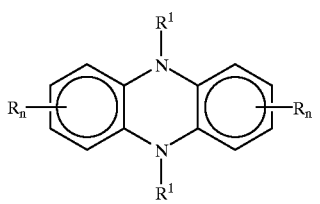

(II)

wherein each R may be the same or different, and is a substituent which does not interfere with the condensation of the respective substituted catechols and 1,2-diaminobenzenes, and if the dihydrophenazine product is further N-alkylated or derivatized, does not interfere with the N-alkylation reaction or other N-derivatization. Thus, the substituents R may not, in general, be groups which react with aromatic amino groups or which react with aromatic hydroxyl groups to an extent which is more rapid than the cyclizing condensation of the latter groups with each other. Thus, oxirane groups, isocyanate groups, cyanate groups, and aziridine groups are not acceptable R substituents.

Examples of suitable R substituents include the most preferred alkyl, cycloalkyl, alkaryl, and aralkyl groups, alkoxy groups, and aryl groups; and may also include such groups as cyano, halo, haloalkyl, aryloxy, nitro, sulfonate, acyl, acyloxy, and the like. Most preferably, the substituents R are $C_{1-20}$ alkyl, $C_{4-20}$ cycloalkyl, $C_{7-20}$ alkaryl, $C_{7-20}$ aralkyl, and $C_{6-20}$ aryl, most preferably methyl, ethyl, propyl, isopropyl, butyl, t-butyl, 2-butyl, 2-ethylhexyl, nonyl, octadecyl, and the like. The alkyl, cycloalkyl, aralkyl, and aryl groups may also contain interspersed heteroatoms, particularly O, S, and N. Two or more of the R groups may also be linked to form a cyclic structure, an aromatic structure, i.e. a fused benzene ring, or the like. R may also be an unsaturated group such as ethenyl, ethynyl, propenyl, propargyl, allyl, ω-hexenyl, norbornenyl, and the like, as well as polyoxyalkyl. The number of R groups may vary, and n may vary from 0 to 4, but is preferably 0, 1 or 2. The R substituents may be further substituted by groups which do not interfere in the respective reactions.

The 5,10 substituents $R^1$ may be the same or different, and may both be hydrogen, in which case the compound H is an N-unsubstituted dihydrophenazine, or may be any group which can be derived by reaction with dihydrophenazine at one or both of the 5,10 positions, including particularly alkyl, cycloalkyl, aralkyl, and the like. Groups such as acyl groups may also be useful, as may also unsaturated groups such as ethenyl, propenyl, ω-hexenyl, norbornenyl, and the like. Preferably, the $R^1$ substituents are hydrogen, methyl, ethyl, propyl, or n-butyl. Yet more preferably, both the 5 and 10 positions bear the same $R^1$ group, for example 5,10-dimethyldihydrophenazine.

The substituents R' may advantageously be groups which promote solubility, particularly groups which promote solubility in polar organic solvents such as those used in electrochromic devices, i.e. propylene carbonate. Examples of the latter groups are salt or salt-forming groups, e.g. ammonium, phosphonium, phosphonate, carboxylate, sulfonate, and the like.

The substituents R' may also advantageously be groups which are polymerizable or copolymerizable, or which can be used to attach the phenazine compound to an existing polymeric or non-polymeric compound or substrate. Examples of such groups are acrylate, epoxy, isocyanate, acrylonitrile, methacrylate, acrylamide, hydroxyl, hydroxyalkyl, vinyldimethylsilyl, mercaptoalkyl, hydroxyaryl, mercaptoaryl, and the like. For example, acrylate-functional dihydrophenazines may be copolymerized with methylacrylate, methylmethacrylate, and other unsaturated monomers to form dihydrophenazine-bearing polymer films. R' groups may also include blocked polymerizable groups which can later be unblocked to generate reactive functionality. The R' groups may also be chromophores and in particular electrochromophores, particularly electrochromic redox active groups such as pyridinium salts and bipyridinium salts.

The subject invention compounds also include those of the formula III and IV:

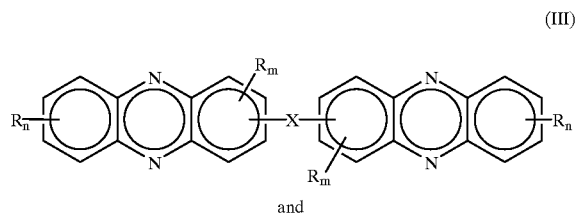

(III)

and

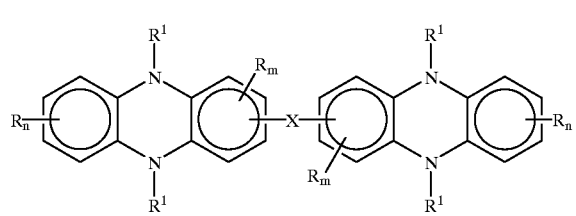

(IV)

where X is a covalent bond or a linking group which is unreactive under the reaction conditions required to form III and IV, e.g., an alkylene, arylene, cycloalkylene, sulfone, keto, ether, or similar linking groups, preferably $C_{1-18}$ alkylene, most preferably methylene, ethylene, isopropylidine, or the like. The linking groups may contain multiple unsaturation, either conjugated or non-conjugated.

The X linking group may also constitute a fused aromatic or alicyclic ring structure, in which case the value of m for the substituents on the ring to which the X linking ring is fused may be 0, 1, or 2. Two examples are:

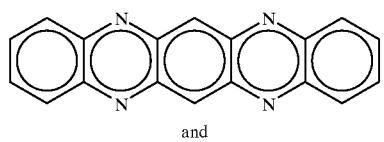

and

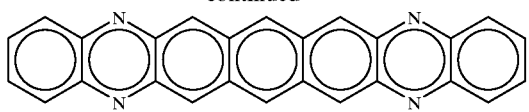

Further phenazines and dihydrophenazines which may be prepared are those having the formula:

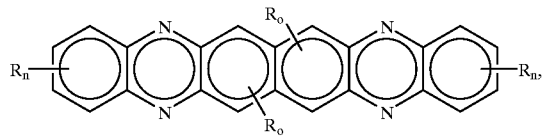

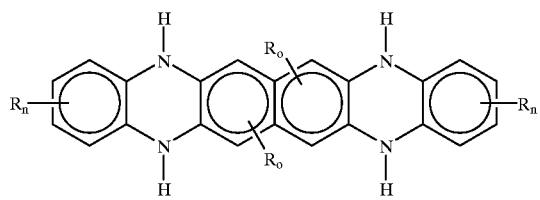

where o is an integer of 0, 1, or 2, and similar structures which may be regarded as

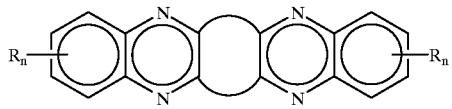

where the circular ring connecting the pyrazine rings represents a fused aromatic structure. An example of the latter is:

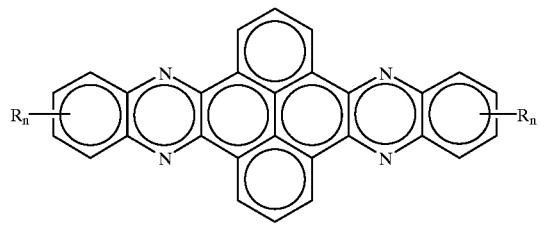

and the corresponding dihydrophenazines.

Preferred compounds of this type are those corresponding to III and IV where the linkages between the phenazine rings are such as to result in compounds such as:

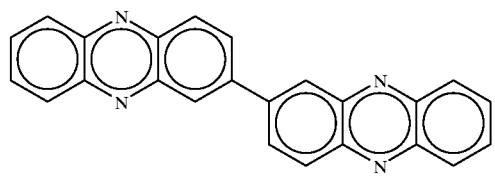

In formulas III and IV, R may be the same as defined for formulas I and II, but m (Formulas III and IV) is 3 or less, preferably 0 or 1.

The subject compounds I and II may be prepared through the solvent mediated reaction between a catechol of the formula (1):

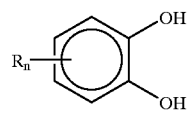

with a 1,2-diaminobenzene of the formula (2):

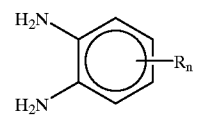

where R and n have been defined previously.

The subject invention compounds III and IV may be prepared from the catechol (I) and a bis(1,2-diaminoaryl) compound, for example one of the formula (3):

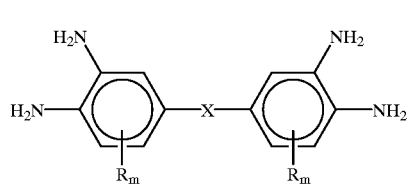

where X is as defined previously, and is preferably a covalent bond. A preferred bis(1,2-diaminoaryl) compound is, for example, 3,3'-diaminobenzidine.

Also capable of preparation by the process of the invention are more complex phenazines and dihydrophenazines having additional fused ring systems derived from fused multi-ring catechol-type derivatives such as:

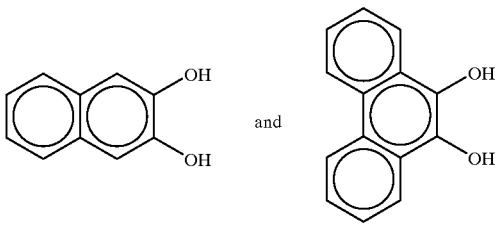 and 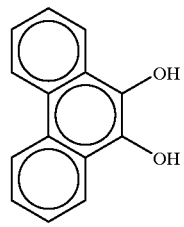

and analogous 1,2-diaminobenzene derivatives.

The reaction between the catechol and the 1,2-diaminobenzene is solvent mediated. In other words, the reaction takes place in the presence of a solvent which allows for reaction without requiring superatmospheric pressure, and which allows for the reaction to be completed within a reasonable period of time, without solidification and without buildup of solid material on the walls of the reaction vessel. The reaction takes place preferably within three days, more preferably within 24 hours, and most preferably in ten hours or less. The solvent is preferably one which will produce a homogenous reaction, and is preferably a polar, protic solvent. It is highly preferred that at the end of the reaction, the product mixture be liquid or contain minimal solids.

Examples of preferred solvents are the higher alcohols, for example n-butanol, n-octanol, 2-ethylhexanol, lauryl alcohol, myristyl alcohol, and the like, and preferably glycols, monomeric polyols such as glycerine, and oligomeric glycol ethers. Suitable glycols include ethylene glycol, 1,2-propylene glycol, 1,3-propanediol, 1,2-butylene glycol, 1,4-butanediol, neopentyl glycol, 1,6-hexanediol, cyclohexanedimethanol, and 1,4-cyclohexanediol. Suitable glycol ethers include diethylene glycol, triethylene glycol, dipropylene glycol, tripropylene glycol, and similar compounds, including their alkyl ether derivatives, particularly their methyl ether and ethyl ether terminated derivatives, e.g. diglyme and diglyet and higher oligomeric analogs thereof. Suitable monomeric polyols include glycerine, trimethylolpropane, glycerol monomethyl ether, and the like. Ethylene glycol, diethylene glycol, propylene glycol, and dipropylene glycol are preferred.

Also useful are polar aprotic solvents such as acetonitrile, N-methylpyrollidone, dimethylformamide, dimethylacetamide, tetrahydrofuran, propylene carbonate, and similar compounds. Other examples of suitable solvents include the xylenes, toluene, etc.

In addition to these solvents, either the diaminoaryl compound or the catechol reactant, when liquid, may be used in excess as the mediating solvent, preferably the latter. In this case, the catechol or diaminoaryl compound must be used in at least a half mole excess over the amount stoichiometrically required to react with the counter-reactant, preferably a one fold molar excess, and most preferably a 1.5 to 4 fold molar excess. In the reaction between the catechol and the 1,2-diaminobenzene compound, it is highly preferable that the solvent be water soluble or water miscible.

The reaction takes place at the lowest temperature which provides an acceptable reaction rate. Suitable temperatures are, in general, greater than 100° C., preferably greater than 150° C., and most preferably above 170° C. Maximum reaction temperature is preferably less than 250° C., more preferably less than 225° C., and when compounds of the formula (2) are used, preferably less than 200° C. For reactions of single ring catechols and single ring 1,2-diaminobenzenes, temperatures in the range of 170° to 190° C. have proven particularly useful. While the temperature is not overly critical, temperatures below 170° C., and particularly below 150° C. provide for only a very slow reaction, while if the temperature is too high, the amount of undesired byproducts is increased significantly.

The solvent is preferably chosen such that the reaction can take place under reflux conditions or at lower temperatures at standard pressure or modestly elevated or reduced pressure. It is one of the benefits of the subject process that pressure vessels need not be used, although their use is not contraindicated. Use of pressure vessels may reduce reaction time, or allow lowering of the reaction temperature. Water is preferably removed while the reaction is progressing. For systems operating under reflux, the water may be removed and condensed in a distillation column. If the solvent and water are immiscible, the solvent may be returned to the reactor. Otherwise, fresh solvent may be added to the reactor to replace solvent lost in the distillation, if necessary. With high boiling solvents where reflux conditions are not established, water may be removed by stripping with a gas stream, for example dry nitrogen. Air cannot be used, in general, unless phenazine is to be prepared. Pressures lower than 1.5 atm absolute are preferred, as these reactions may take place in standard process equipment.

The progress of the reaction may be monitored by measuring the change in concentration of the reactants or by formation of product. When the catechol is used in excess as the mediating solvent, the reaction is best monitored by measuring the disappearance of the 1,2-diaminobenzene compound. When the two reactants are used in stoichiometric ratio in the presence of an organic mediating solvent, the concentration of either reactant may be used to monitor the reaction.

The reaction may be catalyzed. For example, Lewis acid catalysts such as zinc chloride and the like may be useful. The catalyst is preferably one which accelerates the condensation without significantly increasing generation of byproducts and impurities.

Upon completion of the reaction to the degree desired, the product may be isolated or may be further reacted to form 5-substituted, 10-substituted, or 5,10-disubstituted dihydrophenazines, or, if a bis(dihydrophenazine) is produced, the corresponding substituted bis (dihydrophenazine). If isolated as a 5,10-unsubstituted-5,10-dihydrophenazine, the product may be oxidized with air, oxygen, or another oxidizing agent to form the corresponding phenazine. For example, oxidation by sublimation in the presence of oxygen may be used. In this manner, phenazine and a variety of ring-substituted phenazines may be inexpensively prepared in large quantities.

Purification of the reaction mixture generally involves addition of water to remove water soluble impurities, including excess catechol, which is water soluble, and/or 1,2-diaminobenzene, also water soluble, and water soluble solvent. The phenazine and dihydrophenazine products are in general of only limited solubility in water. The product may be washed several times with water, mixtures of water and organic liquids such as ethanol or acetone, or these organic liquids alone.

Potentially the most useful aspect of the present invention is the ability to form 5,10-derivatives of the dihydrophenazines, particularly alkyl or cycloalkyl derivatives, and most preferably dimethyl and diethyl derivatives, by alkylation of the central ring nitrogens with an alkylating agent such as a haloalkane, for example bromomethane or iodomethane, or another alkylating agent such as alkylsulfates, alkyl sulfonates, or trialkyloxonium salts. This reaction may be performed following initial isolation of the dihydrophenazine, or may be done in the same reactor, without first isolating the intermediate.

Derivatization is preferably alkylation, and may take place in solution, for example solution in acetonitrile or similar solvent. Most preferably, the alkylation preferably takes place in a two phase system wherein one of the phases is a solid phase, in the presence of a catalyst belonging to the general category of phase transfer catalysts. Many phase transfer catalysts are suitable, including cyclic polyethers (cryptands), polyethylene glycols, etc. However, phase transfer catalysts such as quaternary ammonium salts, quaternary phosphonium salts, in particular phase transfer catalysts such as tetrabutylammonium iodide, methyltributylammonium chloride, and the like have proven very useful. Derivatization in liquid multiphasic systems, for example aqueous alkali and non-polar organic solvent are also useful.

Derivatizing conditions may be established by those skilled in the art of N-derivatization. In general, when derivatizing agents such as alkylhalide or dialkylsulfates and like compounds are used, a basic inorganic salt such as alkali metal carbonate or bicarbonate are added to scavenge hydrohalic acid or alkyl sulfate acid formed during the reaction. A suitable solvent for the dihydrophenazine should be used. Acetonitrile is preferred, but other polar non-protic solvents such as acetone, dimethylsulfoxide, dimethylacetamide, N-methylpyrollidone, dimethylformamide, and the like may be used as well. Non-polar solvents, such as toluene, xylene, etc., are useful as well. Mixtures of solvents may be used. It is preferred that the solvent be substantially soluble in water, or water miscible. Derivatization by groups such as epoxy groups, isocyanate groups, and the like may be conducted in suitable solvent.

Dihydrophenazines bearing hydrogen at the 5,10 positions are particularly susceptible to oxidation to the corresponding phenazines. Not only would such phenazines contaminate the desired N-substituted dihydrophenazine product, but moreover, the phenazines cannot be N-alkylated, and thus they cannot later be reduced to the desired N-substituted dihydrophenazine. Addition of a reducing agent such as sodium dithionite to the N-derivatization reaction prevents this oxidation, and yet does not interfere with the derivatization. Other non-interfering reducing agents may also be used. Sodium dithionite is preferred, however, and may be present in an amount of from less than 5% of theory based on dihydrophenazine, to about 50% of theory. The dithionite, and basic inorganic salt, when present, form the solid phase of the reaction. Without wishing to be bound to any particular theory, it is believed that the phase transfer catalyst assists in supplying dithionite ions and carbonate into the organic phase, in which the latter inorganic compounds are not particularly soluble.

By the term "a phenazine compound" is meant, generally, a phenazine (no 5,10 substituents), a dihydrophenazine, or a 5- or 10-monosubstituted or 5,10-disubstituted dihydrophenazine, bis(dihydrophenazine), or the like. By the term "1,2-diaminoaryl compound" is meant a compound having at least one substituted or unsubstituted aryl ring bearing vicinal primary amino groups. By the term "a catechol" is meant catechol (i.e. 1,2-dihydroxybenzene) or a substituted and/or fused ring compound containing at least two vicinal hydroxyl groups. The substituents R and $R^1$ of the 1,2-diaminoaryl compound, catechol, or phenazine compound are not generally limited in size, but are preferably $C_{1-20}$ alkyl, $C_{4-12}$ cycloalkenyl, $C_{2-30}$ alkynyl, $C_{7-30}$ alkaryl, $C_{6-30}$ aryl, $C_{7-30}$ aralkyl, and their alkyl, halo, cyano, and other derivatives non-reactive at the reaction conditions, more preferably, $C_{1-8}$ alkyl, $C_{2-10}$ alkenyl, $C_{5-12}$ cycloalkyl, $C_{5-12}$ cycloalkenyl, $C_{2-10}$ alkynyl, and $C_{6-10}$ aryl, $C_{7-20}$ aralkyl, $C_{7-20}$ alkaryl, and most preferably $C_{1-4}$ alkyl, $C_{2-6}$ alkenyl, $C_{2-6}$ alkynl, $C_{5-6}$ cycloalkyl and $C_6$ aryl. These substituents may also include interspersed heteroatoms of N, O, S, or P, for example in heterocyclic substituents, both saturated, unsaturated, and aromatic.

By the term "one pot synthesis" is meant that the synthesis may be carried out in but a single reaction vessel without removing any intermediate products, such as non-N-alkylated 5,10-dihydrophenazines. It would not defeat the purpose of the invention to transfer the intermediate product without further substantial work-up, i.e., without drying, to another reaction vessel. If the reaction could take place in a single reaction vessel of sufficient size, the synthesis should still be considered a one pot synthesis even if more than one reaction vessel is actually used.

Terms such as miscible, immiscible, and sparingly soluble are to be interpreted as one skilled in the art would interpret such terms in similar unit processes. For example, "sparingly soluble" when applied to a wash solvent used for purification of a solid product means that the solubility of the product in the wash solvent is low enough so that any loss of product by solution can be tolerated. Some product/solvent systems may be used cold which would not be considered "sparingly soluble" when warm or hot. Likewise, when adding a solvent of less solvating power for the desired product to a solution of the product in another solvent, the term "miscible means" that the two solvents form a single phase system in the quantities used.

By the term "one fold molar excess" and similar terms is meant one mole of reactant over and above the stoichiometric requirement, referenced to 1.0 mole at stoichiometry. Thus, if 1.0 mole is stoichiometrically required, a one fold molar excess would require 2.0 mole, and a two fold molar excess would require 3.0 mole.

Having generally described this invention, a further understanding can be obtained by reference to certain specific examples which are provided herein for purposes of illustration only and are not intended to be limiting unless otherwise specified.

EXAMPLE 1

To a 12 L Morton flask is charged 702 g 1,2-diaminobenzene and 2.1 Kg catechol (3 equivalents based on 1,2-diaminobenzene). Heat is applied by a heating mantle, and at the end of 30 minutes, all materials are melted and the temperature has risen to 90° C. Over the next 40 minutes, the temperature is increased to ca. 170° C. The temperature is maintained in the range of 151° C. to 187° C. over a 4½ day period. The reaction mixture is cooled to 80° C. and 8 L deionized water added over 30 minutes. The mixture is allowed to cool to room temperature overnight, and a filter candle used to remove water. A further 8 L water is added and heated to 70° C., cooled to 40° C., and the water again removed. A further wash with 8 L water is again performed, with the wash temperature lowered only to 60° C. during removal of water. The product is filtered on a filter funnel and air dried for 30 minutes to yield ca. 1200 g of moist 5,10-dihydrophenazine containing approximately 20% water. Yield of dry 5,10-dihydrophenazine is 960 g (68% of theory, based on 1,2-diaminobenzene).

EXAMPLE 2

To a 12 L flask is added 800 g of the wet filter cake from Example 1, 3.8 L acetonitrile, 275 g sodium dithionite, 868 g sodium carbonate, 1.2 L methyliodide, and 140 g methyltributylammonium chloride. The reaction is heated overnight to approximately 40–70° C. under reflux. TLC of the reaction mixture of this first run shows the reaction is complete.

In a second run, to a 5 L flask are added the same ingredients as in the preceding paragraph, but in half the amounts previously indicated. Approximately 500 mL acetonitrile is removed by distillation and 2 L water added. The flask is cooled to room temperature overnight.

In both flasks, considerable white inorganic materials are visually present. Each flask contains two layers. Half the organic layer from the first flask is combined with the organic layer in the second flask, and 10 L of deionized water added to each flask and stirred for 45 minutes at room temperature. All inorganic materials dissolve, and the product crystallizes. The product from both flasks is collected on a filter funnel, washed with 1 L ethanol, and air dried to yield 1210 g crude 5,10-dimethyldihydrophenazine. A 12 L flask is charged with 1200 g of the crude 5,10-dimethyldihydrophenazine, 6 L toluene, and heated to 80° C. The solution is circulated through a filter bag containing 800 g charcoal G60 for 2 hours. The initially blue solution appears lighter after the charcoal treatment. The solution was decanted and concentrated to 1.8 L by distillation, cooled to 90° C., and 1.8 L ethanol added. The mixture was allowed to cool to room temperature overnight. The solid collected on a filter funnel was washed with 1 L cold ethanol, and oven dried under vacuum at 60° C. for 96 hours to give 783 g (57% yield based on 1,2-diaminotoluene) of light green 5,10-dimethyldihydrophenazine.

EXAMPLE 3

A 100 g sample of 5,10-dihydrophenazine is heated, melted, and sublimed, while a steady stream of oxygen is sparged through the flask. The sublimate is largely phenazine.

EXAMPLE 4

5,10-dihydrophenazine in an amount of 10 g is dissolved in 100 ml ethanol and added to 2.6 g NaOH dissolved in 2 ml of water. The mixture was heated to reflux and $O_2$ bubbled through for 30 minutes. TLC shows that the 5,10-dihydrophenazine is converted completely to phenazine. The mixture was stripped to a volume of 45 ml and 25 ml water added. After cooling in a refrigerator, 8.0 grams of crude phenazine is collected by filtration. The crude phenazine is dissolved in 80 ml toluene, filtered hot, and stripped to 25 ml. When cooled, 5.86 of still somewhat brown phenazine is collected. After an additional recrystallization from toluene, a further toluene solution (50 ml) is treated with 1.0 g charcoal, reduced to 20 ml, cooled to room temperature and then under refrigeration, to yield 4.0 g (40%) of yellow phenazine.

EXAMPLE 5

A 12 L round bottom flask is charged with 427 g 3,4-diaminotoluene and 1085 g 4-methylcatechol (2.5 equivalents based on 3,4-diaminotoluene). To this mixture is added 840 mL ethylene glycol, and the mixture heated to reflux. A nitrogen flow is established through the condenser, from which water in the amount of 35 g is collected. After removal of 40 mL solvent, the temperature of the reaction climbs from 170–183° C. to 210° C. This temperature is maintained by continuing to remove solvent. In all, 200 mL solvent is removed. An additional 500 mL solvent is added and reflux continued at about 206° C. TLC shows the reaction to be almost complete after about 60 hours. The mixture is then quenched and washed with 4.2 L of water, at which point the reaction mixture turns purple. The mixture is heated to 80° C. and cooled to room temperature. Water is removed using a filter candle. The mixture is twice more washed in the same way with 2×8 L water, water being removed from the final wash at 40° C. The product, believed to be a mixture of 2,7-dimethyl-5,10-dihydrophenazine and 2,8-dimethyl-5,10-dihydrophenazine, is not isolated.

EXAMPLE 6

To the wet and unisolated product of Example 5 is added 429 g sodium dithionite, 815 g sodium carbonate, 4.2 L acetonitrile, 1089 mL iodomethane, and 126 g methyltributylammonium chloride. The mixture is heated to reflux and 200 g additional sodium dithionite added after 2 hours. After 7 hours total, 4 L of water is added to quench the reaction mixture and wash the product. The reaction mixture is orange. After cooling to room temperature overnight, water is removed with a filter candle, and two additional washes performed with 2×4 L water. The solid product is collected by filtration and washed with 5 L ethanol. Product in the amount of 816 g is obtained.

The crude product is dissolved in 4 L of toluene at 80° C., and circulated through a filter bag containing charcoal. After 10 minutes, the solution becomes light yellow. After circulation for 1 hour, the filtrate is collected and reduced to 1.0 L by distilling off toluene, is cooled to 80° C., and 1.2 L isopropanol added. The mixture is heated to redissolve the partially crystallized product, and cooled overnight. The product is collected by filtration, washed with cold isopropanol/ethanol (1:1), and dried for 24 hours under vacuum at 60° C. to give 397 g (50% overall yield based on 3,4-diaminotoluene) of what is believed to be a mixture of 2,5,7,10-tetramethyldihydrophenazine and 2,5,8,10-tetramethyldihydrophenazine as an off-white solid.

EXAMPLE 7

To a 300 mL 2-neck round bottom flask is added 10.0 g 3,4-diaminotoluene and 40.8 g (3 equivalents based on 3,4-dianminotoluene) of 4-t-butyl-catechol, and heated to 170° C. for 4 hours, at which time TLC indicated that the reaction was complete. To the cool reaction mixture was added 200 mL of 1:4 acetone/water. After cooling to 80° C., the slow filtering solid, believed to be a mixture of 2-methyl-7-t-butyl-5,10-dihydrophenazine and 2-methyl-8-t-butyl-5,10-dihydrophenazine, was isolated.

To a 300 mL round neck flask was added 11.0 g of the mixture of 2-methyl-7-t-butyl-5,10-dihydrophenazine and 2-methyl-8-t-butyl-5,10-dihydrophenazine prepared immediately above, 7.6 g sodium dithionite, 10.2 g sodium carbonate, 100 mL acetonitrile, 15 mL iodomethane, and 1 mL each of methyltributylammonium chloride and water, and heated to reflux. After 4 hours, TLC indicated completion of the reaction. Water in the amount of 150 mL was added, and 20 g of moist, light brown product separated by filtration. TLC showed the presence of t-butylcatechol and a phenazine product in addition to the desired product. The solid was dissolved in 100 mL acetonitrile and refluxed, cooled, and the recrystallized product washed with cold acetonitrile and cold ethanol to give 2.8 g gray solid. The filtrate was stripped and cooled to isolate 2.3 g of a second crop of crystals. Product identity as a mixture of 2,5,10-trimethyl-7-t-butyldihydrophenazine and 2,8,10-trimethyl-8-t-butyldihydrophenazine was confirmed.

EXAMPLE 8

A bis(dihydrophenazine) was prepared by reacting 10.0 g 3,3'-diaminobenzidine with 34.7 g (2 fold excess) of 4-methylcatechol in 40 mL of ethylene glycol at reflux for 24 hours at ca. 212° C., following which the temperature dropped to 203° C. and reflux continued, with removal of a small amount (5 mL) of ethylene glycol, for an additional 24 hours. The product was precipitated by addition of water and washed with 3×250 mL water at 80° C. The product was separated by filtration, yielding 25.0 g of a mixture of 7,8'-bis(2-methyl-5,10-dihydrophenazine) and 8-(8'-(3'-methyl-5',10'-dihydrophenazinyl))-2-methyl-5,10-dihydrophenazine:

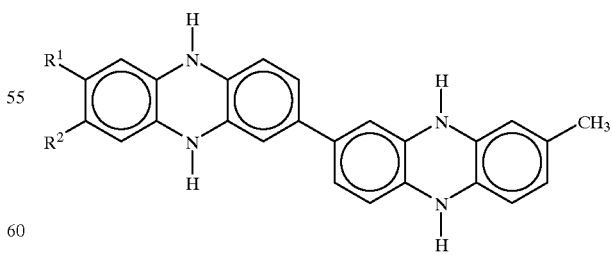

where $R^1$ and $R^2$ are H and $CH_3$ or $CH_3$ and H, respectively.

A 1 L round bottom flask is changed 20.0 g of the product prepared immediately above, 26.3 g sodium dithionite, 26.5 g sodium carbonate, 250 mL acetonitrile, 5 mL water, 5 g methyltributylammonium chloride, and 31 mL methyl iodide. The initially black reaction mixture becomes yellow after 24 hours reflux. Stirring is stopped, and an additional 200 mL acetonitrile and 20 mL iodomethane are added. Following additional refluxing, 250 mL water is added, the mixture cooled, and the solid isolated by filtration. The isolated solid is dissolved in 500 mL hot toluene, stirred with 12 g charcoal for 2 hours, and filtered. The filtrate was stripped to 100 mL and cooled in a refrigerator. The solid precipitate was collected by filtration and washed with ethanol to give 7.94 g (38% of theory) of the 5,5',10,10'-tetramethyl derivatives of the bis(dihydrophenazines).

EXAMPLE 9

In a manner similar to Example 8, substituted bis(5,10-dihydrophenazines) were prepared from 10.0 g 3,3'-diaminobenzidine and 34.7 g 3-methyl catechol in ethylene glycol, to form 37.4 g of the solid bis(dihydrophenazine) product. The product was methylated with MeI as before. The 5,10,5',10'-tetramethylated product was first isolated as a black oil which was recrystallized after extracting several times with hexane to produce a yellow solid.

In a similar manner, other dihydrophenazines and bis (dihydrophenazines) were prepared, having the following structures. The electrochromic behavior and wavelength of maximum absorption for the oxidized compounds are given in Table I. Redox potentials (E1) are given in mV referenced to 5,10-dimethyldihydrophenazine as a standard (E1$_{DMP}$= 300 mV). Compounds 1, 2, 7, 8, 11, 13, and 14 contained isomers in which the ring substituents of the left-most aryl rings are reversed top to bottom.

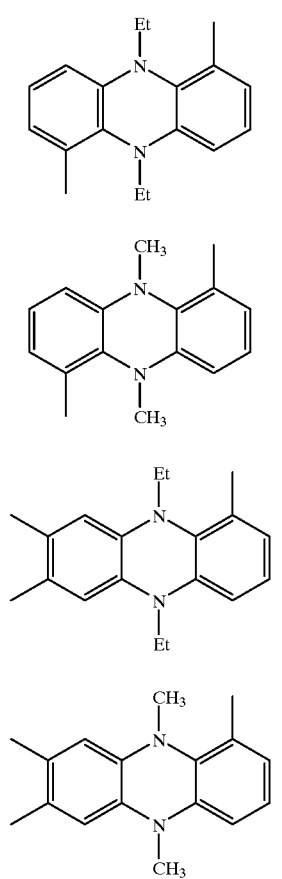

(1)

(2)

(3)

(4)

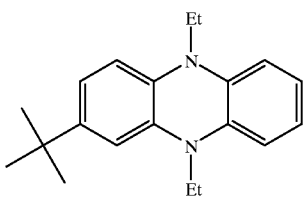

(5)

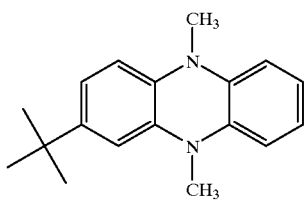

(6)

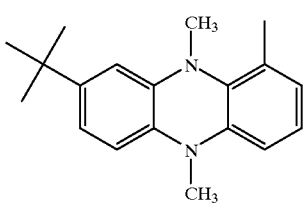

(7)

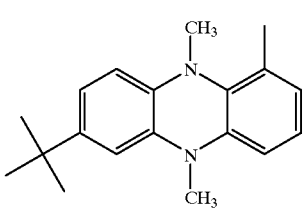

(8)

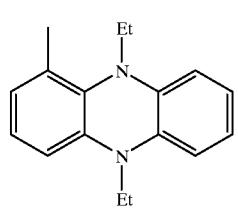

(9)

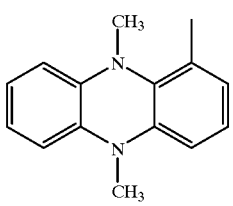

(10)

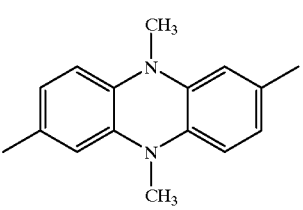

(11)

-continued

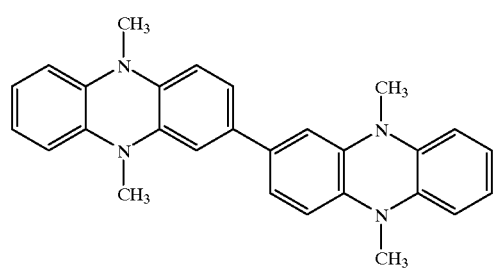

(12)

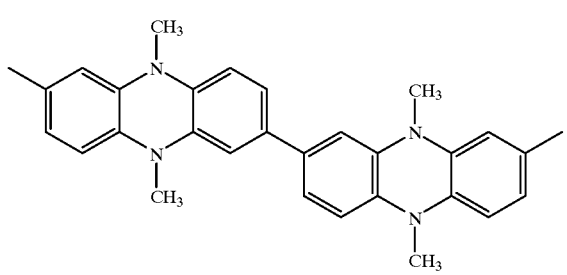

(13)

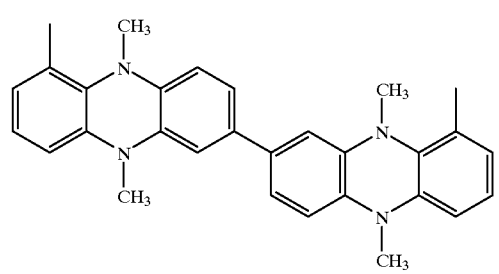

(14)

TABLE I

| Compound | E1 | λ$_{max}$ |
|---|---|---|
| 1 | 524 | — |
| 2 | 504 | 502 |
| 3 | 304 | — |
| 4 | 240 | 504 |
| 5 | 188 | 472 |
| 6 | 252 | 472 |
| 7 | 348 | — |
| 8 | 300 | 490 |
| 9 | 392 | — |
| 10 | 348 | 480 |
| 11 | 192 | — |
| 12 | 236 (348) | — |
| 13 | 200 (308) | — |
| 14 | 280 (376) | — |

Having now fully described the invention, it will be apparent to one of ordinary skill in the art that many changes and modifications can be made thereto without departing from the spirit or scope of the invention as set forth herein.

What is claimed is:

1. A process for the preparation of a phenazine group-containing compound, comprising the steps of:
   providing a 1,2-diaminoaryl compound and a catechol, wherein either the 1,2-diaminoaryl compound or the catechol is provided in at least 50% molar stoichiometric excess;
   reacting the 1,2-diaminoaryl compound with the catechol; and
   obtaining a 5,10-dihydrophenazine group-containing compound.

2. The process of claim 1, wherein said catechol is provided in at least 50% molar stoichiometric excess.

3. The process of claim 1, wherein said 1,2-diaminoaryl compound is provided in at least 50% molar stoichiometric excess.

4. The process of claim 1, further comprising the step of providing an organic solvent having a boiling point in the range of 170° C. to about 250° C. at the pressure at which the reaction is conducted.

5. The process of claim 1, further comprising the step of providing an aliphatic glycol.

6. The process of claim 1, wherein said catechol is provided in at least a one fold stoichiometric excess.

7. The process of claim 1, further comprising the step of removing water during said reacting step.

8. The process of claim 1, wherein said catechol comprises a catechol of the formula:

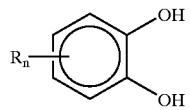

wherein R is a substituent which is unreactive under the reaction conditions and n is an integer from 0 to 4, or where two or more of R are linked together in an aryl or cycloaliphatic ring system; and wherein said 1,2-diaminoaryl compound is a 1,2-diaminoaryl compound of the formula:

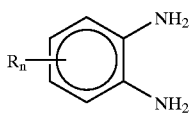

where R is a substituent which is unreactive under the reaction conditions and n is an integer from 0 to 4, or where two or more of R are linked together in an aryl or cycloaliphatic ring system, or wherein said 1,2-diaminoaryl compound contains two or more

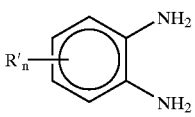

groups linked together by a covalent bond or by an intervening organic linking group non-reactive under the reaction conditions wherein n' is an integer of 0 to 3.

9. The process of claim 8, wherein said R groups of said catechol and said 1,2-diaminoaryl compound are independently selected from the group consisting of alkyl, alkenyl, alkynyl, cycloalkyl, cycloalkenyl, aryl, aralkyl, alkaryl, alkoxy, and polyalkyleneoxy.

10. The process of claim 8, wherein said R groups of said catechol and said 1,2-diaminoaryl compound are selected from the group consisting of cyano, nitro, halo, acyl, acyloxy, and alkylester groups.

11. The process of claim 8, wherein R is selected from the group consisting of hydrogen and $C_{1-8}$ alkyl.

12. The process of claim 1, wherein said obtaining step includes the steps of:

adding water;

precipitating the 5,10-dihydrophenazine group-containing compound; and washing the 5,10-dihydrophenazine group-containing compound with water or an organic solvent in which the same is insoluble or sparingly soluble.

13. The process of claim 1, further comprising the steps of subliming said 5,10-dihydrophenazine group-containing compound in an oxygen containing gas stream and recovering the corresponding phenazine.

14. The process of claim 1, further comprising the steps of reacting the 5,10-dihydrophenazine group-containing compound with an N-derivatizing agent at least one of the 5 and 10 positions to produce a 5-substituted, 10-substituted, or 5,10-disubstituted dihydrophenazine.

15. The process of claim 14, wherein said N-derivatizing agent comprises an alkylating agent.

16. The process of claim 15, wherein said alkylating agent comprises an alkylhalide, dialkylsulfate, alkylsulfonate, or trialkyloxomium salt.

17. The process of claim 14, wherein said 5,10-dihydrophenazine is not isolated prior to said reacting with said N-derivatizing agent.

18. The process of claim 14, wherein said reacting takes place in a polyphasic reaction containing minimally two phases, in the presence of a phase transfer catalyst.

19. The process of claim 14, wherein said N-derivatizing takes place in the presence of a compatible reducing agent which reduces phenazine to dihydrophenazine.

20. The process of claim 19, wherein said reducing agent comprises sodium dithionite.

21. The process of claim 18, wherein at least one phase comprises a solution of the dihydrophenazine reactant in water miscible organic solvent.

22. The process of claim 21, wherein a second, solid phase is present.

23. The process of claim 18, wherein an aqueous phase and a non-polar organic liquid phase are present.

24. The process of claim 21, wherein said solvent comprises acetonitrile.

25. A process for the preparation of a phenazine group-containing compound, comprising the step of reacting:

a) a one fold molar stoichiometric excess or more of a catechol having the formula (1)

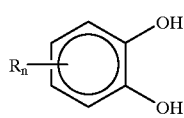

(1)

wherein R is an alkyl group or two or more of R are linked to form an aryl or cycloaliphatic ring system, and n is 0–4, with b) a 1,2-diaminoaryl compound of the formula (2) or (3):

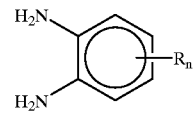

(2)

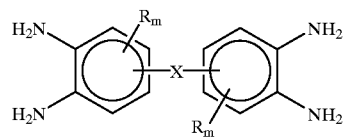

(3)

where R and n have been defined previously, where m is an integer from 0 to 3, and where X is a covalent bond or an organic linking group which is unreactive at the reaction conditions, to obtain a 5,10-dihydrophenazine or mixture of 5,10-dihydrophenazines corresponding to the formula:

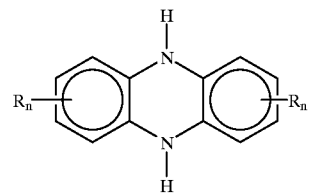

when (2) is employed, and corresponding to the formula:

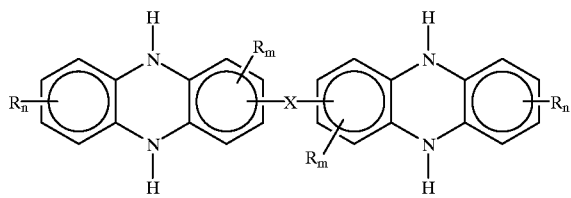

when (3) is employed.

26. The process of claim 25, wherein said reaction takes place at a temperature of from about 150° C. to about 250° C.

27. The process of claim 25, wherein an organic solvent which boils in the range of 150° C. to 250° C. at the reaction pressure is added to the reactants a) and b).

28. The process of claim 27, wherein said solvent is an alkylene glycol, an oligomeric polyalkylene glycol, or an alkyl ether of an alkylene glycol or oligomeric polyalkylene glycol.

29. The process of claim 27, wherein said solvent comprises ethylene glycol.

30. The process of claim 25, wherein water is removed during the course of the reaction.

31. The process of claim 25, further comprising precipitating said dihydrophenazine, washing said dihydrophenazine with water, an organic solvent in which said dihydrophenazine is only sparingly soluble, or a mixture of said organic solvent and water, and alkylating or acylating said dihydrophenazine at one or more of the 5,10- and/or 5',10'-positions to form an N-alkyl or N-acyldihydrophenazine corresponding to the formula:

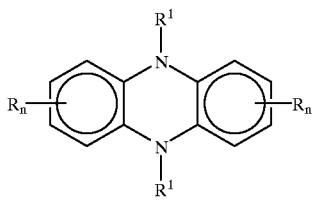

wherein each $R^1$ independently is hydrogen or an alkyl, cycloalkyl, alkenyl, at least β-unsaturated cycloalkenyl, at least β-unsaturated alkynyl, acyl, or aralkyl group, and at least one $R^1$ is not hydrogen, or a dihydrophenazine of the formula:

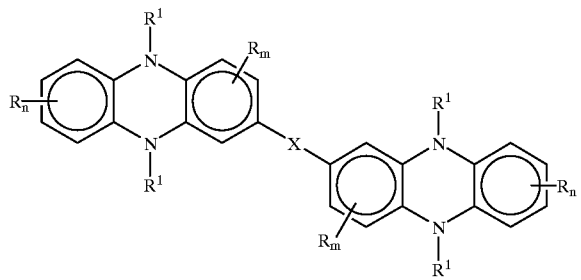

wherein $R^1$ is defined as before, and at least one $R^1$ is not hydrogen.

32. The process of claim 31, wherein said alkylating takes place in an at least two phase reaction mixture, in the presence of a phase transfer catalyst and a reducing agent effective to prevent oxidation of dihydrophenazine to phenazine.

33. The process of claim 25, wherein said catechol is selected from the group consisting of catechol, 3-($C_{1-8}$ alkyl)catechol, and 4-($C_{1-8}$ alkyl)catechol.

34. The process of claim 25, wherein said 1,2-diaminoaryl compound is selected from the group consisting of 1,2-diaminobenzene, 3-($C_{1-8}$alkyl)-1,2-diaminobenzene, 4-($C_{1-8}$ alkyl)-1,2-diaminobenzene, and 3,3'-diaminobenzidene.

35. A one pot process for the synthesis of a 5-substituted, 10-substituted, or 5,10-dihydrophenazine or bis(5,10-dihydrophenazine) substituted at one or more of the phenazine nitrogen atoms, said process comprising:

a) introducing into a reaction vessel a 1,2-diaminoaryl compound corresponding to the formula (2) or (3):

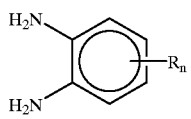
(2)

where each R independently is a substituent which is non-reactive under the synthesis conditions and n is an integer from 0 to 4;

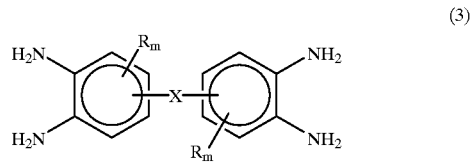
(3)

where each R independently is as defined above and each m independently is an integer of 0 to 3; and wherein X is a covalent bond or an organic linking group unreactive under the synthesis conditions, or X is an aromatic ring system fused to at least one ring at adjacent positions and m is 0 to 3 on each respective ring to which said aromatic ring system is fused;

b) introducing into said reaction vessel a catechol corresponding to the formula (1)

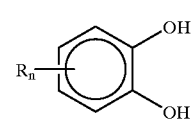
(1)

where R is as previously defined, n is an integer of 0–4, or where two or more $R_n$ are linked together into an aromatic or cycloaliphatic ring structure, wherein said catechol is present in greater than a one fold molar excess based on the 1,2-diaminoaryl compound, or an organic solvent is present, or said catechol is present in stoichiometric excess and an organic solvent is present;

c) heating the reaction vessel containing a) and b) until the reaction reaches a desired degree of completion to obtain an impure mixture of dihydrophenazine(s);

d) purifying said impure mixture of dihydrophenazine(s) by washing with a liquid in which said catechol and said 1,2-diaminoaryl compound are soluble but said dihydrophenazine is only sparingly soluble to obtain a purified dihydrophenazine;

e) alkylating said purified dihydrophenazine(s) in a reaction mixture containing an amount of a reducing agent effective to prevent oxidation of said dihydrophenazine (s) to the corresponding phenazine(s); and f) recovering an alkylated dihydrophenazine or bis (dihydrophenazine) alkylated at least at one of the phenazine nitrogen ring positions.

36. The process of claim 35, further comprising purifying said alkylated dihydrophenazine or bis(dihydrophenazine) by dissolving said alkylated dihydrophenazine or said alkylated bis(dihydrophenazine) in organic solvent to form a solution, contacting said solution with an impurity-removing carbon product; separating a purified solution from said carbon product by filtration; and recrystallizing a purified alkylated dihydrophenazine or alkylated bis (dihydrophenazine) product from said purified solution.

37. The process of claim 36, wherein said recrystallization is effected in whole or in part through addition of a miscible solvent in which said alkylated dihydrophenazine is insoluble or sparingly soluble.

38. The process of claim 35, wherein said organic solvent is an alkylene glycol, an oligomeric glycol, or an alkyl ether of an alkylene glycol or an oligomeric polyalkylene glycol.

39. The process of claim 1, further comprising the step of providing an organic solvent.

40. A process for the preparation of a phenazine group-containing compound, comprising the steps of:

providing a 1,2-diaminoaryl compound and a catechol, wherein either the 1,2-diaminoaryl compound or the catechol is provided in excess to, in turn, facilitate their reaction at or below a pressure of about 1.5 atmospheres;

reacting the 1,2-diaminoaryl compound with the catechol at or below a pressure of about 1.5 atmospheres; and obtaining a 5,10-dihydrophenazine group-containing compound.

41. The process according to claim 40, wherein either the 1,2-diaminoaryl compound or the catechol is provided in at least 50% molar stoichiometric excess.

42. The process according to claim 40, wherein the step of reacting the 1,2-diaminoaryl compound with a catechol occurs in non-pressure processing equipment.

43. A process for the preparation of a phenazine group-containing compound, comprising the steps of:

providing a 1,2-diaminoaryl compound and a catechol, wherein either the 1,2-diaminoaryl compound or the catechol is provided in excess to, in turn, facilitate their reaction in non-pressure processing equipment;

reacting the 1,2-diaminoaryl compound with a catechol in non-pressure processing equipment; and obtaining a 5,10-dihydrophenazine group-containing compound.

44. A 5,10-dihydrophenazine group-containing compound prepared in accordance with the process of claim 1.

45. A 5,10-dihydrophenazine group-containing compound prepared in accordance with the process of claim 25.

46. A 5,10-dihydrophenazine group-containing compound prepared in accordance with the process of claim 35.

47. A 5,10-dihydrophenazine group-containing compound prepared in accordance with the process of claim 40.

48. A 5,10-dihydrophenazine group-containing compound prepared in accordance with the process of claim 43.

49. A process for the preparation of a phenazine group-containing compound, comprising the steps of:

providing a 1,2-diaminoaryl compound and a catechol, wherein either the 1,2-diaminoaryl compound or the catechol is provided in at least 50% molar stoichiometric excess;

providing a reaction mediating solvent from the at least 50% molar stoichiometric excess of either the 1,2-diaminoaryl compound or the catechol;

reacting the 1,2-diaminoaryl compound with the catechol; and obtaining a 5,10-dihydrophenazine group-containing compound.

* * * * *